United States Patent [19]

Markham et al.

[11] Patent Number: 4,517,177

[45] Date of Patent: May 14, 1985

[54] METHOD OF COMBATTING PLANT DISEASES

[75] Inventors: Peter G. Markham; Rodney Townsend; Jeffrey W. Davies, all of Norwich, England

[73] Assignee: National Research Development Corporation, London, England

[21] Appl. No.: 330,859

[22] Filed: Dec. 15, 1981

[30] Foreign Application Priority Data

Dec. 17, 1980 [GB] United Kingdom ............... 8040438
Apr. 1, 1981 [GB] United Kingdom ............... 8110117

[51] Int. Cl.$^3$ .................... A61K 39/12; A61K 37/00; A01N 63/00
[52] U.S. Cl. ......................................... 424/93; 424/89
[58] Field of Search .................... 424/93, 89; 47/1

[56] References Cited

PUBLICATIONS

Townsend et al., J. of Bacteriology, vol. 142, No. 3, pp. 973-981 (1980).
Cole et al., "Spiroplasmaviruses", pp. 451-464.

*Primary Examiner*—Blondel Hazel
*Attorney, Agent, or Firm*—Oblon, Fisher, Spivak, McClelland & Maier

[57] ABSTRACT

Yellows diseases have devastated crops, particularly of citrus fruit. They are associated with (and ostensibly caused by) very small mycoplasma or spiroplasma type organisms (MLO for short). Attempts at chemical control of MLOs have been unsuccessful. The present invention is based on a remarkable new finding that biological control can be achieved by introducing into the phloem of the plant a virus which is infective to the MLO. The invention is of particular interest in relation to diseases associated with *Spiroplasma citri*, especially in citrus plantations.

8 Claims, 1 Drawing Figure

METHOD OF COMBATTING PLANT DISEASES

BACKGROUND OF THE INVENTION

1. Field of the Invention

This invention relates to combatting certain yellows diseases in plants.

2. Description of the Prior Art

The "yellows" are a well known group of plant diseases occurring in temperate and tropical regions. They are found in over 300 genera of plants including monocotyledons and dicotyledons, trees and herbaceous plants. Yellows diseases have caused serious economic losses in long-term crops, for example peach, cherry, pear, citrus fruits and coconuts. Lethal yellowing of palms has wiped out the Jamaican coconut industry and has devastated plantations in Haiti, Cuba, Ghana, Nigeria and Florida, U.S.A. The disease aster yellow is particularly destructive and has caused major losses of crops in the U.S.A., including lettuce, carrots, celery, potatoes and flax. In continental Europe the apple proliferation disease is causing considerable problems.

Most of the yellows diseases are associated with Mycoplasma-like organisms (MLO). The term "Mycoplasma-like organism" or MLO, wherever occurring in this specification, is used in a broad sense to cover yellows disease-associated organisms of the family Mycoplasmataceae or Spiroplasmataceae. The term "Mycoplasma" is used in a narrower sense to refer to the genus of the same name with the family Mycoplasmataceae. The following chart indicates classification:

| CLASS: | MOLLICUTES |
| --- | --- |
| Order: | Mycoplasmatales. |
| Family I: | Mycoplasmataceae |
| Genus I: | Mycoplasma |
| Genus II: | Ureaplasma |
| Family II: | Acholeplasmataceae |
| Genus: | Acholeplasma |
| Family III: | Spiroplasmataceae |
| Genus: | Spiroplasma |
| Species: | *Spiroplasma citri* |
| | Corn stunt spiroplasma and many others not yet fully characterised |

MLO are very small organisms, of diameter typically from 300 nm to 1 micron, and are the smallest known cells capable of independent multiplication. Instead of having a rigid cell wall like bacteria they have a triple-layered plasma membrane typically 7-11 nm thick. MLO occur in the phloem of plants but not in other parts of the plant tissue. While mycoplasmas are of variable shape, spiroplasmas adopt a helical shape when constrained to do so, e.g. by osmotic pressure effects when they are contained in plant phloem.

Until the late 1960s it was thought that yellows diseases were caused by viruses. In the 1970s many of them were shown to be associated with MLO. Attempts have been made to treat the disease by use of chemicals, for example tetracycline. In a paper given by Markham to the British Crop Protection Conference in 1977, a review was made of possible future trends in combatting yellows diseases. It was suggested that chemical control and the breeding of resistant MLO were the most promising approaches.

SUMMARY OF THE INVENTION

It has now surprisingly been found the MLO-associated yellows diseases can be combatted effectively by introducing into the phloem of the plant a virus which is infective to the MLO, i.e. for which the MLO is a host. The method of the invention is likely to be applicable to MLO in general, but its application to *Spiroplasma citri* is of particular interest.

DESCRIPTION OF THE INVENTION

*Spiroplasma citri* is phytopathogenic causing citrus stubborn disease and infecting a wide range of herbaceous hosts. Cultures of *S. citri* frequently produce up to four morphologically distinct types of virus-like particles, three of which have been shown to be authentic Spiroplasma viruses by their ability to form plaques on lawns of colonies of sensitive Spiroplasma strains. They have been designated SVC1, SVC2 and SVC3. They are described in various papers by Cole et al and in "The Atlas of Insect and Plant Viruses", ed. K. Maramorosch (1977), pages 451-464. The normal carrier state of these viruses is uncertain. They may be temperate, existing in the majority of cells as prophages; or a pseudolysogenic condition may prevail, in which viruses multiply slowly within the organisms but do not cause cell death. Despite the relative abundance of Spiroplasma viruses, even in cultures made directly from infected plants, viruses have never, to the applicants' knowledge, been observed in association with Spiroplasmas within the cells of infected plants. Particles resembling viruses have been seen apparently attached to the outer surface of cells of organisms which might be MLO and which occurred in a few yellows diseased plants. Since, however, these organisms have so far resisted all attempts to grow them in cell-free media, it has not been possible to determine whether the viruses originate from an MLO, some other organism, or the host plants. Consequently their biological significance has remained a subject for conjecture. It has now been found that viruses are produced by *S. citri*, strain SP-A within the cells of host plants infected with this strain and that virus infection has a marked effect on the production of disease symptoms, which, surprisingly, is a beneficial effect.

*S. citri* strain SP-A produces small numbers of extracellular polyhedral virus particles, 40×35 nm with a short tail 15 nm long, typical of SVC3. The SVC3 virions are distinctive because they emerge from infected Spiroplasmas within buds of membrane although this outer layer is lost before attachment to a host cell. It has previously been shown that particles resembling SVC3 occur with a low frequency in primary cultures made from plants infected with strain SP-A, but extensive examination of thin sectional material from these plants has never revealed the presence of similar particles in the phloem vessels to which Spiroplasmas are confined or in any other tissues.

It is within the concept of the invention that most MLO found in plants will be cultivatable to produce small quantities of a virus for which they act as host, and that infection of plant with this or a similar virus will combat the disease associated with the MLO.

The preferred method of introducing the virus is by use of a culture containing the MLO and the virus. This can be used to infect insects, such as leafhoppers, which, in turn, infect the plant. Alternatively it is possible to inoculate the plant phloem directly. The infection can be spread by insects or by parasitic plants such as the vine-like dodder (*Cuscuta Spp.*). Plant phloem tissue infected by any of these means can then be grafted from plant to plant. The virus-containing MLO replicate in the infected plants, thus provided source of further material for grafting.

The invention includes particularly a method of combatting or inhibiting a yellows disease which comprises grafting onto a diseased or disease-susceptible plant, phloem tissue containing a virally infected MLO associated with the disease, in which the virus is derived by cultivating an MLO obtained from another plant (whether of the same plant species or not) having a yellows disease associated with the same MLO. It is possible that some degree of cross-resistance will occur, i.e. that culture from one strain of MLO will protect the plants against infection by the same and several other strains of MLO.

Also included within the invention is plant tissue comprising phloem containing virus capable of infecting and MLO, i.e. a virus for which an MLO is a host, especially such tissue containing a virally infected MLO (in which virus particles are present within cells of the MLO). It will be appreciated, that plant phloem containing an MLO having virus particles apparently merely attached to its outer surface, in accordance with one possible explanation of the observations previously made on plants which have not been infected with a pre-identified virus, would not be part of the invention. In the present invention, we are concerned with a virus which invades the cells of the MLO. The invention is, of course, particularly applicable to combatting disease in citrus fruits which is associated with *Spiroplasma citri*. It includes particularly citrus plant tissue containing a virally infected *Spiroplasma citri* organism.

Examples

The following Examples illustrate the invention:

Chart of the experimental method

1. Orange trees infected with citrus little-leaf disease
   ↓
2. Isolate of *Spiroplasma citri*
   ↓
3. Cloned isolate of *Spiroplasma citri* strain SP-A
   | injection into insects;
   | release of the insects to infect
   | *Vinca rosea* plants
   ↓
4. *Vinca rosea* plants infected with the *Spiroplasma citri* strain 5. Isolate ("SP-V3") of *Spiroplasma citri* from one *Vinca rosea* plant
   | direct
   | inoculation of a shoot
   | of *Vinca rosea* with culture
   | from the isolate "SP-V3"
   ↓
6. Shoot containing the inoculum
   | grafting onto *Vinca rosea*
   | infected with *Spiroplasma citri*
   ↓
7. *Vinca rosea* plant showing resistance to infection with *Spiroplasma citri*
   | grafting of the resistant
   | *Vinca rosea* plant
   ↓
8. *Vinca rosea* plants in which the virus-containing cells of *Spiroplasma citri* are seen to have multiplied.

EXAMPLE 1

"Lop-sided" fruits from sweet orange trees (*Citrus sinensis* cv. Valencia) with little-leaf disease were washed and surface-sterilized with 70% (v/v) alcohol. The aborted seeds were then removed aseptically and rinsed in sterile water. Seed coats were selected for study because it is known that the citrus stubborn agent may be cultured from this tissue. They were ground with sand in Saglio growth medium [Saglio et al., C.r. hebd. Séanc. Acad. Sci. Paris, 272, 1387 (1971)], containing the selective agent "Floxapen" (Beecham) 50 micrograms/cm$^3$. The extracts were then centrifuged at 500 g for 2 minutes to remove debris and filtered through sterile 'Millipore' membrane filters (0.45 micron pore diameter). The filtrate was diluted with further growth medium and incubated at 32° C. Portions were also streaked and incubated on plates of medium solidified with 1% agar ('Tonagar' No. 2; Oxoid).

The resulting culture (stage 2 on the chart) was cloned by the usual method of removing the relevant organisms and re-culturing several times. The resulting cloned isolate (stage 3 on the chart) was cloned by the usual method of removing the relevant organisms and re-culturing several times. The resulting cloned isolate (stage 3 on the chart) contained *Spiroplasma citri* strain SP-A (National Collection of Plant Pathogenic Bacteria, Ministry of Agriculture, Food and Fisheries, Harpenden, England, NCPPB 2565).

Leafhopper insects (*Euscelis plebejus*) are known to be vectors for MLO-associated diseases in plants, Markham et al, Ann. appl. Biol. 78, 49 (1974). Leafhoppers were injected with inoculum from a sub-culture of the cloned isolate as follows. The needles used for injection were hand-drawn from glass tubing (4 mm o.d. and 2 mm i.d.) to give an orifice about 10–20 microns in diameter and were sterilized by heating for 2 hours at 160° C. Inoculum was forced through the needle by a peristaltic pump, giving a flow rate of 0.5 cm$^3$/min. About $2 \times 10^4$ colony-forming Spiroplasma units were introduced into each insect. Adult leafhoppers were anaesthetized with carbon dioxide, placed in an adjustable, multiple, insect holder similar to that described by Maramorosch and Jernberg, Journal of Economic Entomology, 63, 1216 (1970), and injected between the third and fourth abdominal sternites. *Vinca rosea* (Madagascar periwinkle) plants were then exposed to these insects and showed the usual symptoms of infection (stage 4 on the chart). These plants become infected after a time dependent on the temperature at which they are kept, in this case after 3–4 weeks at 30° C.

Leaves of one of the *V. rosea* plants were then ground with sand in Saglio medium. Solids were filtered to give a primary isolate which we have designated "SP-V3" on the chart. This isolate SP-V3 was then stored at −20° C. As hereinafter mentioned, a sub-cultured of "SP-V3" has been deposited in a culture collection.

Sub-cultures from the isolate SP-V3 were used in an experimental procedure for the direct inoculation of *V. rosea*. It is notoriously difficult to inoculate a substance into the phloem of a plant. When the phloem is damaged it seals itself up. The technique employed comprises maintaining an open-pore condition between phloem cells by immersing phloem-containing plant tissue in a medium comprising a chemical agent which brings about this effect (in this case ethylenediamine tetraacetic acid and 2-mercaptoethanol), cross-sectioning the phloem while maintaining it in this medium and then contacting a free end of the phloem with the inoculum under conditions conducive to or creating flow of the inoculum into and along the phloem. This technique is of general applicability to the direct inoculation of substances in general into plant phloem in general.

The inoculation was carried out in repli-plates. The *V. rosea* plants were kept in the dark for 3 days beforehand, in order to use up their nutrients. They were then transferred to a dimly lit laboratory. Long straight stems were selected and denuded of all leaves (except for a small part of the petiole at the base). The stems were sterilized with 70% (v/v) ethanol. Three cuttings 5.5 cm. long were made and each cutting was laid horizontally across 3 chambers of a repli-plate. Chambers 2 and 3 were sealed off from each other by a seal of petroleum jelly. Chambers 1 and 2 remained in communication, i.e. in effect as a single chamber. Into chamber 3 was introduced a sterile solution of phosphate buffer (pH 7) containing 2.5 mM E.D.T.A. In chambers ½ the same solution but containing also 10 mM 2-mercaptoethanol was introduced. The solutions covered the cuttings. With the ends of the cuttings still covered, they were cut with a razor blade about 1 mm. from each end. The solutions were then removed and very quickly chamber ½ was filled with phosphate buffer containing 0.2 M sucrose plus *S. citri* culture (obtained from a sub-culture of isolate SP-V3), to give a final concentration of $10^6$ to $10^7$ colony-forming units/$cm^3$. Chamber 3 was re-filled with sufficient (4 ml.) of the same solution of starting phosphate buffer and E.D.T.A. to cover the cuttings. The repli-plates were then covered and left in the dark at 25° C. for 8–10 hours. The cuttings were then removed and placed on paper tissue soaked with tap water.

The ends of the inoculated cuttings (scions) were trimmed to a V-shape and side-grafted into stems of *V. rosea* plants. The technique of side-grafting is described in "The Grafter's Handbook" by R. J. Garner (1958), page 162. Only 4 out of 9 grafts "took", all on the same plant. The other two test plants bearing the other 5 grafts showed no sign of infection. The infected plant showed unusually mild symptoms of the disease. The leaves were only slightly chlorotic and a little smaller than usual; flowers, although small, continued to form and no wilting occurred. Electron microscopy revealed evidence of extensive multiplication of a virus of appearance similar to that of SVC3 in the spiroplasmas contained within the phloem vessels. The normally helical cells were distorted and swollen and contained numerous full and empty virus-like particles. Enveloped particles could be seen budding from infected cells and naked virions were widely distributed in the phloem. Full and empty particles could be seen attached to spiroplasma membranes but not to the phloem cell membrane. No virus particles were detected outside the phloem vessels.

The accompanying drawing is a reproduction of an electron micrograph of sections of phloem in a petiole of a periwinkle plant. The main body of the reproduction shows spiroplasma cells which have been infected with the SP-V3 culture of *S. citri.* The host spiroplasma cells contain numerous complete (1) and incomplete (2) virus particles. When newly-formed virions begin to emerge from the cells, a bud-like protrusion forms. Such virions (3) are enveloped by cell membrane. However, the virons attach themselves in a naked form (4) to the membrane of spiroplasma cells which they are about to invade. The bar line represents 0.25 micron. The top right-hand corner of the reproduction shows a cross-section through spiroplasma cells which have not yet been invaded and therefore infected by the virus. At this stage the spiroplasma cells (5) are surrounded by many naked virions (6) attached to the cell membrane. The bar line represents 0.05 micron.

The electron microscopy of ultra-thin sections was carried out as follows. Pieces of young infected leaf material were severed and immediately immersed in 2% glutaraldehyde in 0.05 M cacodylate buffer, pH 7.0, at room temperature and trimmed to 1 mm. After 1–3 days, pieces were transferred to cacodylate buffer, then left overnight, washed in buffer and treated for 1 hour with 1% osmium tetroxide in veronal-acetate buffer at room temperature. The pieces were then washed in distilled water, dehydrated in alcohol saturated with uranyl acetate and left overnight in water-free acetone containing uranyl acetate. After washing in propylene oxide they were embedded in "Epon 812". The blocks were sectioned using an LKB Ultrotome-1 using glass knives. Sections, either silver-gold (c. 60–80 nm) or violet-blue (c. 150–200 nm), were poststained with lead acetate and examined in a Siemens Elmiskop 1A electron microscope.

Sap extracts were prepared by grinding approximately 200 mg of young leaf tissue in 3 $cm^3$ of Saglio culture medium and filtering through 0.22 micron pore diameter sterile 'Millipore' filters. The filtrates were diluted 1,000 fold in culture medium and 20 microliter samples spotted onto lawns of *S. citri* strain SP-A which were incubated at 32° C. After 5 days, small (1.5–3 mm) diameter plaques developed. They were clear in the centre and surrounded by a peripheral zone of turbidity typical of plaques produced by SVC3 virus, Cole et al., Science, 198, 1262 (1977), and which are thought to be lytic in character. The concentration of virus was found to be $5\times10^6$ plaque-forming units (pfu) per g of material of which only a very small proportion was phloem tissue. No plaques were produced by extracts from healthy *V. rosea* plants.

Spiroplasmas could readily be cultured from this plant, but a large proportion were partially or completely non-helical and many were deformed outswellings of the cytoplasmic membrane. These isolates grew more slowly than SP-A or SP-V3 and released numerous SVC3 type particles. Diluted filtrates of these cultures gave rise to typical SVC3 plaques on lawns of SP-A equivalent to a concentration of $1\times10^5$ pfu/$cm^3$. Filtrates from sub-cultures of SP-V3 did not produce plaques on lawns of SP-A or SP-V3.

In order to confirm that the marked reduction in symptom severity was a direct consequence of virus infection, a challenge experiment was performed. Ten *V. rosea* plants were grafted with shoots, showing symptoms, from a plant infected with the lethal strain SP-A from isolate SP-V3. They were maintained at 30° C., at which temperature the concentration of Spiroplasmas in the aerial parts of infected *V. rosea* reaches a maximum concentration 14 days after grafting with *S. citri.* Fifteen days later, shoots from the SP-V3-infected plant (stage 7 on the chart) were grafted onto five of these plants and five healthy plants. After 12 weeks at 30° C. four of the five *V. rosea* plants grafted only with SP-V3-infected shoots had very mild symptoms and no wilting. The graft failed to "take" on the fifth plant which remained symptomless. Those plants which received both grafts showed some leaf yellowing on the branches where the first grafts were made but the rest of the foliage had only very mild symptoms. Four of the plants which did not receive the SP-V3 graft died within 8 weeks, the fifth developed extremely severe symptoms and died after 10 weeks. Spiroplasmas were cultured from all the plants but only those which had received grafts of SP-V3 material yielded cultures in which significant quantities of virus were produced. Observations on the surviving *V. rosea* plants (stage 8 on the chart) were continued for six months but no increase in symptom severity was noted. Indeed, some plants appeared superficially to be completely healthy. However, Spiroplasmas could still be cultured from them.

It is concluded that virus replication can occur in Spiroplasmas within the tissues of host plants and that the consequent loss of Spiroplasma viability, which is manifested in vitro by the production of plaques on lawns of strain SP-A, results in dramatic reduction in the severity of symptoms.

EXAMPLE 2

In a further experiment, *V. rosea* plants were grafted with shoots from the inoculated *S. citri*-resistant *V. rosea* plant (stage 7 on the chart) and these further plants were kept at 30° C. They showed more obvious evidence of the disease but continued to survive. Electron microscopy of sections of plant phloem showed Spiroplasmas heavily infected with a rod-shaped virus similar in appearance to SUC3-like virions were no longer present, however. It appears that the high temperature has resulted in a decline of the SVC3-like virus and expression of the SVC1-like virus. It was concluded that the SVC1-like virus also confers resistance to the *S. citri* infection.

The invention includes a culture of *Spiroplasma citri* strain SP-A which when inoculated in a plant infected with said *Spiroplasma citri* strain expresses SVC1-like and/or SVC3-like virus particles. It includes particularly a culture of the substantially pure isolate SP-V3 hereinbefore mentioned. A freeze-dried sample of such a culture has been deposited with the National Collection of Industrial Bacteria, Torry Research Station, P.O. Box 31, 135 Abbey Road, Aberdeen AB9 8DG, Scotland on Mar. 31st 1981, under the number NCIB 11644. The SVC1-like and SVC3-like virus particles appear to be present in such cultures in a latent form.

We claim:

1. A method of combatting a yellows disease associated with a mycoplasma-like organism (MLO) in a plant, characterised by introducing into the phloem of the plant a virus capable of growing in the MLO; said virus being associated with *Spiroplasma citri* and being capable, when introduced into the plant phloem, of imparting to the plant resistance to the MLO-associated disease.

2. A method according to claim 1 characterised in that the MLO is of the *Spiroplasma citri* species.

3. A method according to claim 2 characterised in that the plant is a citrus species.

4. A method according to claim 1, 2, or 3 characterised in that the virus is SVC1 virus or SVC3 virus as expressed when *Spiroplasma citri* NCIB 11644 is inoculated into the plant phloem.

5. A method according to claim 1 characterised in that plant phloem tissue infected with said virus is grafted onto a plant to be treated.

6. A method according to claim 2 characterised in the the MLO is of the *Spiroplasma citri* species strain SP-A.

7. A method of combatting a yellows disease associated with *Spiroplasma citri* strain SP-A in a plant, characterised by introducing into the phloem of the plant a SVC-1 or SVC-3 virus, said introduction being effected by infecting insects with the virus or by inoculating the plant phloem directly.

8. The method of claim 7 wherein the virus is introduced by grafting plant phloem tissue infected with the virus onto the plant.

* * * * *